(12) United States Patent
Liu et al.

(10) Patent No.: US 12,207,961 B2
(45) Date of Patent: Jan. 28, 2025

(54) METHOD AND APPARATUS FOR CORRECTING BLOOD FLOW VELOCITY ON THE BASIS OF INTERVAL TIME BETWEEN ANGIOGRAM IMAGES

(71) Applicant: SUZHOU RAINMED MEDICAL TECHNOLOGY CO., LTD., Suzhou (CN)

(72) Inventors: Guangzhi Liu, Suzhou (CN); Zhiyuan Wang, Suzhou (CN); Wei Dai, Suzhou (CN); Lin Chen, Suzhou (CN)

(73) Assignee: SUZHOU RAINMED MEDICAL TECHNOLOGY CO., LTD., Suzhou (CN)

( * ) Notice: Subject to any disclaimer, the term of this patent is extended or adjusted under 35 U.S.C. 154(b) by 402 days.

(21) Appl. No.: 17/587,264

(22) Filed: Jan. 28, 2022

(65) Prior Publication Data

US 2022/0151579 A1 May 19, 2022

Related U.S. Application Data

(63) Continuation of application No. PCT/CN2019/120328, filed on Nov. 22, 2019.

(30) Foreign Application Priority Data

Jul. 31, 2019 (CN) .......................... 201910704330.1
Nov. 20, 2019 (CN) .......................... 201911138512.3

(51) Int. Cl.
*A61B 6/00* (2024.01)
*A61B 6/50* (2024.01)
(Continued)

(52) U.S. Cl.
CPC .............. *A61B 6/481* (2013.01); *A61B 6/504* (2013.01); *G06T 7/0016* (2013.01); *G06T 7/20* (2013.01); *G06T 2207/30104* (2013.01)

(58) Field of Classification Search
CPC ....... A61B 6/481; A61B 6/504; G06T 7/0016; G06T 7/20; G06T 2207/30104
See application file for complete search history.

(56) References Cited

U.S. PATENT DOCUMENTS 10,052,158 B2 * 8/2018 Taylor .................... G06V 10/40
10,111,633 B2 * 10/2018 Nickisch ................ A61B 6/463
(Continued)

FOREIGN PATENT DOCUMENTS

CN 103839281 A 6/2014
CN 105559810 A 5/2016
(Continued)

OTHER PUBLICATIONS

Supplementary European Search Report dated Jun. 30, 2023 for Application No. EP 19939547.
(Continued)

*Primary Examiner* — Khai M Nguyen
(74) *Attorney, Agent, or Firm* — Ladas & Parry LLP

(57) ABSTRACT

The present disclosure provides a method for correcting a resting blood flow velocity on the basis of an interval time between angiogram images, comprising: acquiring, in an angiography state, an average blood flow velocity $V_h$ from a coronary artery inlet to a distal end of a coronary artery stenosis (S100); acquiring a time difference $\Delta t$ between start times of two adjacent bolus injections of contrast agent (S200); obtaining a correction coefficient K according to the time difference $\Delta t$ (S300); obtaining a resting blood flow velocity $V_j$ according to the correction coefficient K and the average blood flow velocity $V_h$ (S400), as well as an apparatus configured for implementing the above method. The disclosure obtains the resting blood flow velocity $V_j$ according to the correction coefficient K and the average blood flow velocity $V_h$.

8 Claims, 12 Drawing Sheets

(51) Int. Cl.
*G06T 7/00* (2017.01)
*G06T 7/20* (2017.01)

(56) References Cited

U.S. PATENT DOCUMENTS

| | | |
|---|---|---|
| 2013/0172734 A1 | 7/2013 | Hsieh |
| 2013/0225958 A1 | 8/2013 | Ichihara et al. |
| 2018/0330507 A1 | 11/2018 | Schormans et al. |
| 2024/0289956 A1* | 8/2024 | Takahashi .............. A61B 6/504 |

FOREIGN PATENT DOCUMENTS

| | | |
|---|---|---|
| CN | 108550189 A | 5/2018 |
| CN | 108186038 A | 6/2018 |
| CN | 107978371 A | 7/2018 |
| CN | 108245178 A | 9/2018 |
| CN | 109805949 A | 5/2019 |
| WO | 2015041312 A1 | 3/2017 |

OTHER PUBLICATIONS

Andreas Fieselmann et al: "Interventional 4-D C-Arm CT Perfusion Imaging Using Interleaved Scanning and Partial Reconstruction Interpolation", IEEE Transactions on Medical Imaging, vol. 31, No. 4, Apr. 1, 2012 (Apr. 1, 2012), pp. 892-906, XP055563610, USA ISSN: 0278-0062, DOI: 0.1109/TMI.2011.2181531.
International Search Report for International Application PCT/CN2019/120328 mailed Apr. 20, 2020.
First Chinese Office Action for counterpart application 201910704330.1 Mar. 19, 2020.
Second Chinese Office Action for counterpart application 201910704330.1 Oct. 15, 2020.
The Decision on Japan Patent Grant for JP21560PCT, Japanese patent application 2022-505584 issued on Mar. 7, 2023.

* cited by examiner

METHOD AND APPARATUS FOR CORRECTING BLOOD FLOW VELOCITY ON THE BASIS OF INTERVAL TIME BETWEEN ANGIOGRAM IMAGES

CROSS REFERENCE TO RELATED APPLICATIONS

This application is a continuation of International Patent Application No. PCT/CN2019/120328 filed on Nov. 22, 2019, which claims the benefit of priority from the Chinese Patent Applications Nos. 201910704330.1 filed Jul. 31, 2019 and 201911138512.3 filed Nov. 20, 2019. The entire contents of the aforementioned patent applications are incorporated herein by reference.

TECHNICAL FIELD

The present disclosure relates to the field of coronary artery medical technology, and in particular to a method and an apparatus for correcting blood flow velocity on the basis of an interval time between angiogram images, a coronary artery analysis system and a computer storage medium.

BACKGROUND

The influence of abnormal coronary microcirculation function on myocardial ischemia has gradually attracted attention. The coronary artery system is composed of epicardial coronary arteries and microcirculation.

Generally speaking, the degree of epicardial coronary artery stenosis greater than or equal to 50% can lead to insufficient blood supply to the myocardium, which is clinically diagnosed as coronary heart disease. However, clinical studies have shown that abnormal coronary microcirculation may also lead to insufficient blood supply to the myocardium.

The coronary microcirculation refers to the blood circulation between arterioles and venules, and is the place where blood and tissue cells exchange substances. Studies have shown that although the coronary blood flow reaches TIMI3 level after successful percutaneous coronary interventional surgery, nearly 30% of patients still have abnormal microvascular function, leading to a poor prognosis. Therefore, with the continuous deepening of research, people gradually realize that abnormal coronary microvascular is an important mechanism for the pathophysiology of many heart diseases, and it is necessary to accurately evaluate a functional state of coronary artery microcirculation.

An index of microcirculatory resistance (IMR) of coronary is an indicator of evaluating the functional state of the coronary artery microcirculation.

A contrast agent itself also has a dilation effect on blood vessels. As early as 1959, researchers found that after injecting a contrast agent into coronary arteries of dogs, the quantity of coronary blood flow would increase by 60%, suggesting that the contrast agent can induce partial hyperemia in the coronary artery microcirculation. In 1985, a study found that intracoronary injection of 76% of diatrizoate meglumine in patients with borderline coronary artery disease can significantly increase the pressure difference across the lesion; in 1995, researchers further determined that 59% of the maximum quantity of blood flow can be obtained after intracoronary injection of 8 ml iodixanol 270, and only 94% of the maximum quantity of blood flow can be obtained after intracoronary injection of adenosine 200 ug; by 2003, the microcirculatory hyperemia effect of contrast agents was largely clarified, but slightly weaker than that of other classic vasodilators. Subsequent studies have found that the osmotic pressure of the contrast agent can promote the opening of potassium channels in vascular endothelial cells, which in turn causes the dilation of coronary microcirculation.

Based on these pharmacological effects of the contrast agent, clinical experts have discussed using the contrast agent instead of adenosine to induce microcirculatory hyperemia, which specific operations are similar to the intracoronary administration route of adenosine and the like.

At present, a dosage of 5-10 ml contrast agent is used in most studies. After injecting the contrast agent, it takes an average time of 12-30 s that the coronary microcirculation restores from the hyperemia state to a baseline state. When performing a coronary artery examination, the surgeon will perform angiography from different body position angles for the detected blood vessels. Since it is different about the durations for adjusting the C-arm of an angiography machine to the specified angle each time, and it is also different about the start times for angiography, so that flow velocity during each angiography is affected by the fact that whether the coronary microcirculation after previous angiography restores to the baseline state.

SUMMARY

The present disclosure provides a method and an apparatus for correcting blood flow velocity and microcirculation parameters on the basis of angiogram images, so as to mitigate the problem in the prior art, i.e., the influence of whether the coronary microcirculation after previous angiography restores to the baseline state on the flow velocity during angiography.

In order to achieve the foregoing objectives, in a first aspect, the present disclosure provides a method for correcting a resting blood flow velocity on the basis of angiogram images comprising:

acquiring, in an angiography state, an average blood flow velocity $V_h$ from a coronary artery inlet to a distal end of a coronary artery stenosis;

acquiring a time difference $\Delta t$ between start times of two adjacent bolus injections of a contrast agent;

obtaining a correction coefficient K according to the time difference $\Delta t$;

obtaining a resting blood flow velocity $V_j$ according to the correction coefficient K and the average blood flow velocity $V_h$.

Optionally, in the above method for correcting the blood flow velocity on the basis of angiogram images, a manner for obtaining a resting blood flow velocity $V_j$ according to the correction coefficient K and the average blood flow velocity $V_h$ comprises:

obtaining the resting blood flow velocity $V_j$ according to the formula $V_j=V_h/K$.

Optionally, in the above method for correcting the blood flow velocity on the basis of angiogram images, a manner for obtaining a correction coefficient K according to the time difference $\Delta t$ comprises:

if $\Delta t \geq 30$ s, then K=1;
if $20 \leq \Delta t < 30$ s, then $1 \leq K \leq 1.5$;
if $10 < \Delta t < 20$ s, then $1.5 < K < 2.0$;
if $\Delta t \leq 10$ s, then K=2.

Optionally, in the above method for correcting a resting blood flow velocity on the basis of angiogram images, a manner for acquiring, in an angiography state, an average blood flow velocity $V_h$ from a coronary artery inlet to a distal end of the coronary artery stenosis comprises:

acquiring the number of frames of coronary angiogram images contained in a heartbeat cycle region;

$$V_h = \frac{L}{N/fps};$$

wherein, L represents a length of a blood vessel through which a contrast agent flows in the heartbeat cycle region; N represents the number of frames of the coronary angiogram images contained in the heartbeat cycle region; and fps represents the number of frames transmitted per second.

Optionally, in the above method for correcting a resting blood flow velocity on the basis of angiogram images, a value range for L is 50-150 mm; or L=100 mm.

Optionally, in the above method for correcting a resting blood flow velocity on the basis of angiogram images, a manner for measuring the average blood flow velocity $V_h$ comprises: contrast agent traversal distance algorithm, Stewart-Hamilton algorithm, First-pass distribution analysis method, optical flow method, or fluid continuity method.

In a second aspect, the disclosure provides a method for correcting a maximum dilated blood flow velocity on the basis of angiogram images comprising:

the above method for correcting a resting blood flow velocity on the basis of angiogram images;

acquiring a maximum dilated blood flow velocity according to the resting blood flow velocity $V_j$.

Optionally, in the above method for correcting a maximum dilated blood flow velocity on the basis of angiogram images, a manner for acquiring a maximum dilated blood flow velocity according to the resting blood flow velocity $V_j$ comprises:

acquiring the maximum dilated blood flow velocity according to the formula $V_{max}=aV_j+b$;

wherein $V_{max}$ represents the maximum dilated blood flow velocity, and a represents a constant with a value ranging from 1 to 3, and b represents a constant with a value ranging from 50 to 300.

In a third aspect, the disclosure provides a method for correcting coronary microcirculation vascular evaluation parameters on the basis of angiogram images, comprising:

acquiring an average pressure $P_a$ at a coronary artery inlet in a heartbeat cycle region according to the angiogram images;

acquiring a pressure drop $\Delta P$ from the coronary artery inlet to a distal end of the coronary artery stenosis;

obtaining the corrected coronary microcirculation vascular evaluation parameters according to the maximum dilated blood flow velocity $V_{max}$ obtained by the above method for correcting a resting blood flow velocity on the basis of angiogram images, as well as $\Delta P$ and $P_a$.

In a fourth aspect, the present disclosure provides an apparatus for correcting a blood flow velocity on the basis of angiogram images, for using in the above method for correcting a resting blood flow velocity on the basis of angiogram images, comprising: a first blood flow velocity unit, a time difference unit, a correction coefficient unit and a second blood flow velocity unit. The first blood flow velocity unit is connected to the second blood flow velocity unit, and the correction coefficient unit is connected to the time difference unit and the second blood flow velocity unit, respectively.

The first blood flow velocity unit is configured to acquire, in an angiography state, an average blood flow velocity IA from a coronary artery inlet to a distal end of a coronary artery stenosis.

The time difference unit is configured to acquire a time difference $\Delta t$ between start times of two adjacent bolus injections of a contrast agent.

The correction coefficient unit is configured to receive the time difference $\Delta t$ transmitted by the time difference unit to obtain a correction coefficient K.

The second blood flow velocity unit is configured to receive the average blood flow velocity $V_h$ in the angiography state sent by the first blood flow velocity unit and the correction coefficient K sent by the correction coefficient unit, and to obtain the resting blood flow velocity $V_j$ according to the correction coefficient K and the average blood flow Velocity $V_h$.

In a fifth aspect, the present disclosure provides an apparatus for correcting a maximum dilated blood flow velocity on the basis of angiogram images, for using in the above method for correcting a maximum dilated blood flow velocity on the basis of angiogram images, comprising: the above apparatus for correcting a blood flow velocity on the basis of angiogram images, and a third blood flow velocity unit connected to the above apparatus for correcting a blood flow velocity on the basis of angiogram images.

The third blood flow velocity unit is configured to acquire the maximum dilated blood flow velocity according to the resting blood flow velocity $V_j$.

In a sixth aspect, the present disclosure provides a coronary artery analysis system comprising a base body, a blood pressure acquisition device and the above apparatus for correcting a maximum dilated blood flow velocity on the basis of angiogram images, both the last two being arranged on the base body.

In a seventh aspect, the present disclosure provides a computer storage medium having stored thereon a computer program to be executed by a processor, wherein the aforementioned method for correcting a resting blood flow velocity on the basis of angiogram images is implemented when the computer program is executed by the processor.

The solutions provided by embodiments of the present disclosure bring about beneficial effects that at least comprise:

The present disclosure provides a method for correcting a blood flow velocity on the basis of angiogram images, which comprises obtaining a correction coefficient K according to a time difference $\Delta t$; and obtaining a resting blood flow velocity $V_j$ according to the correction coefficient K and the average blood flow velocity $V_h$, so as to mitigate, in the prior art, the influence of whether the coronary microcirculation after previous angiography restores to the baseline state on the flow velocity during angiography.

BRIEF DESCRIPTION OF DRAWINGS

The drawings illustrated here are used to provide a further understanding of the present disclosure and constitute a part of the present disclosure. The exemplary embodiments and the descriptions thereof are used to explain the present disclosure, and do not constitute an improper limitation on the present disclosure. In the drawings.

Figure 14:
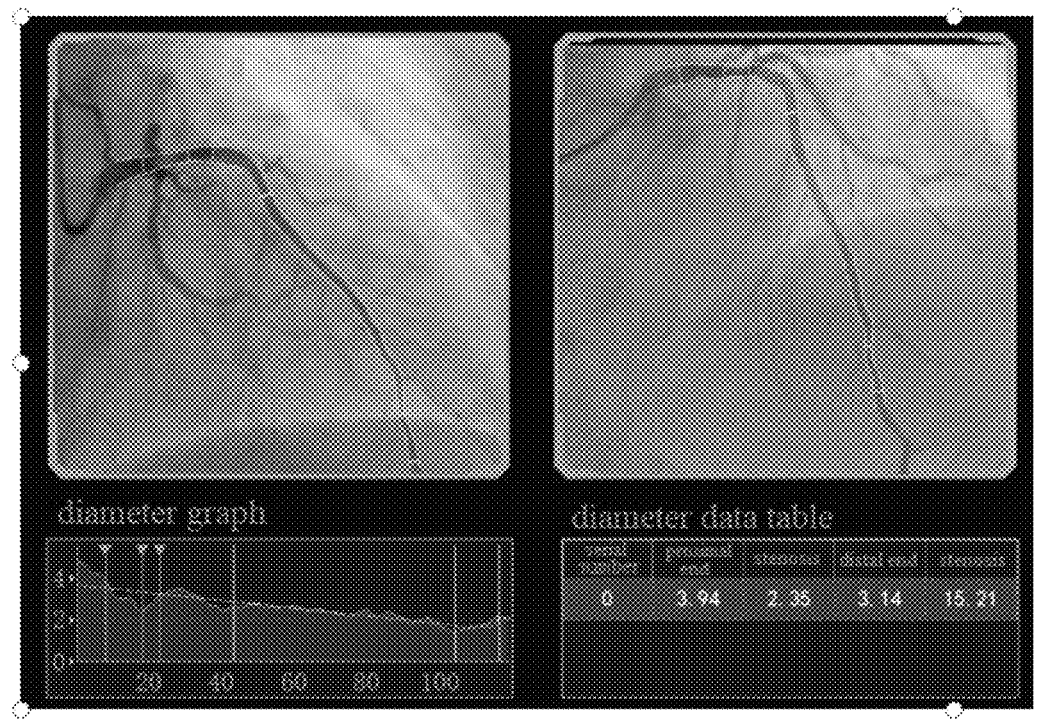
Figure 15:
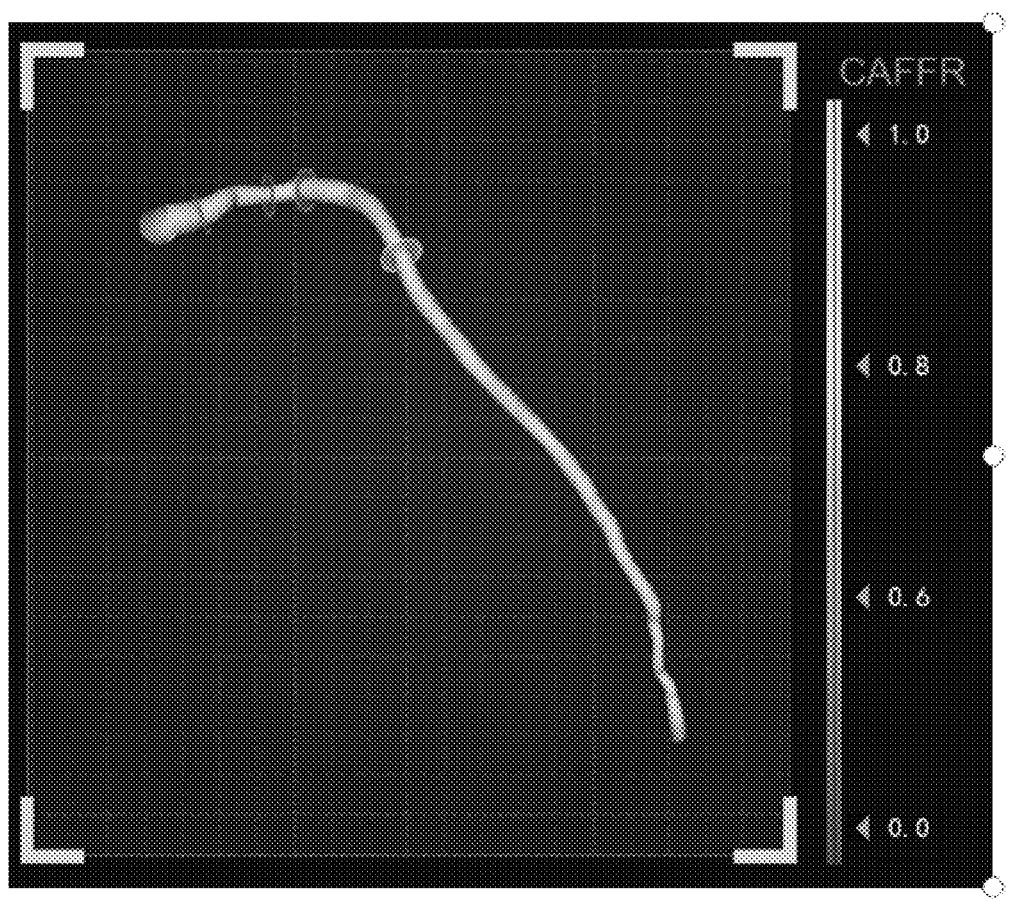
Figure 16:
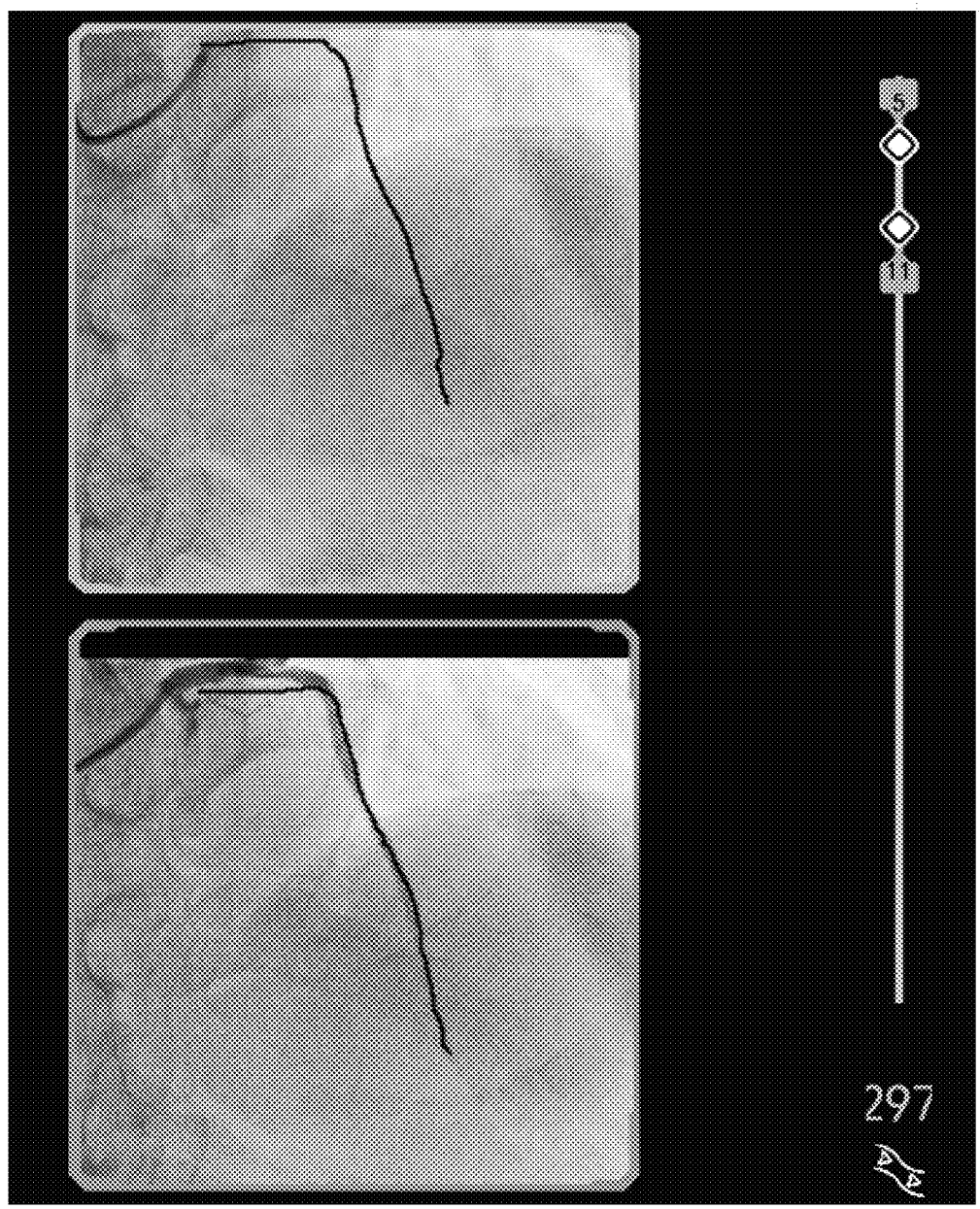
Figure 17:
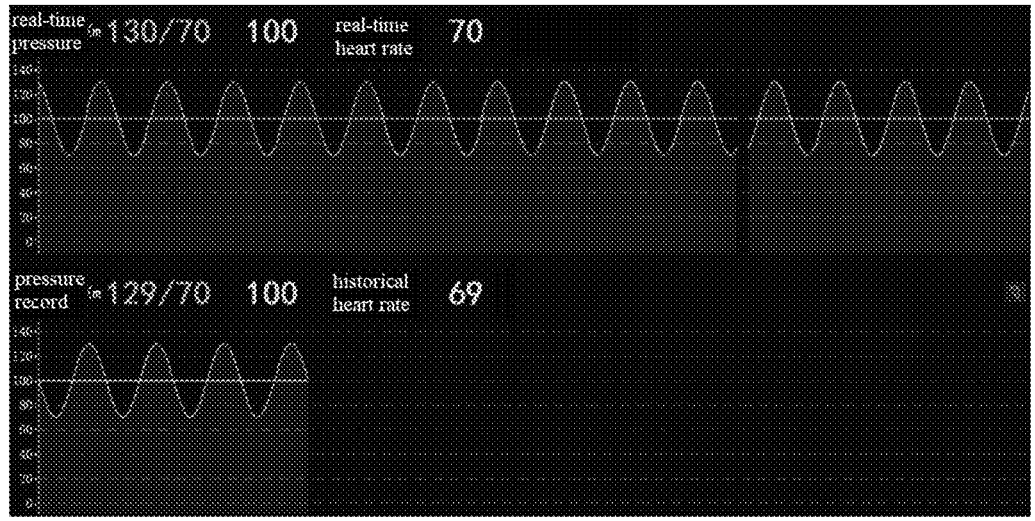
Figure 18:
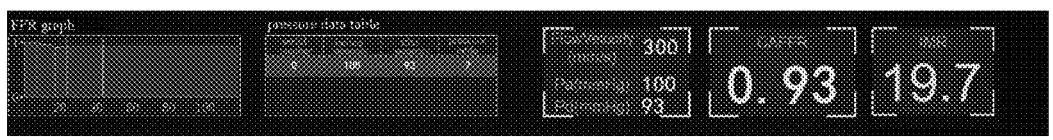
Figure 19:
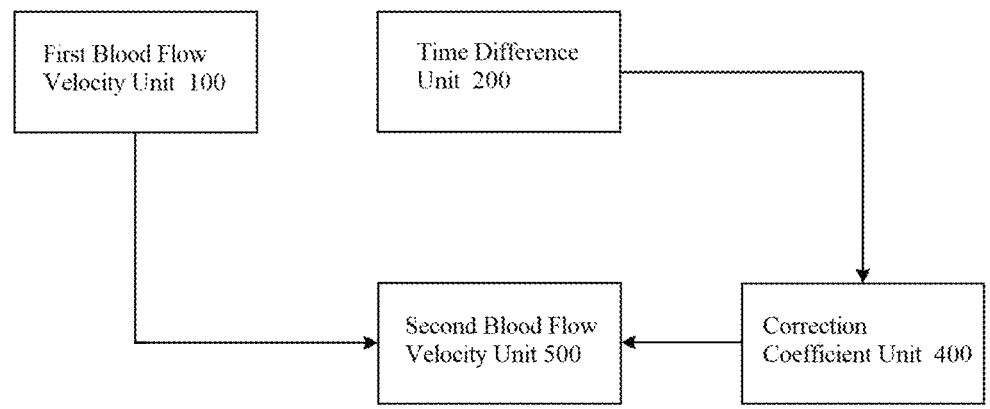
Figure 20:
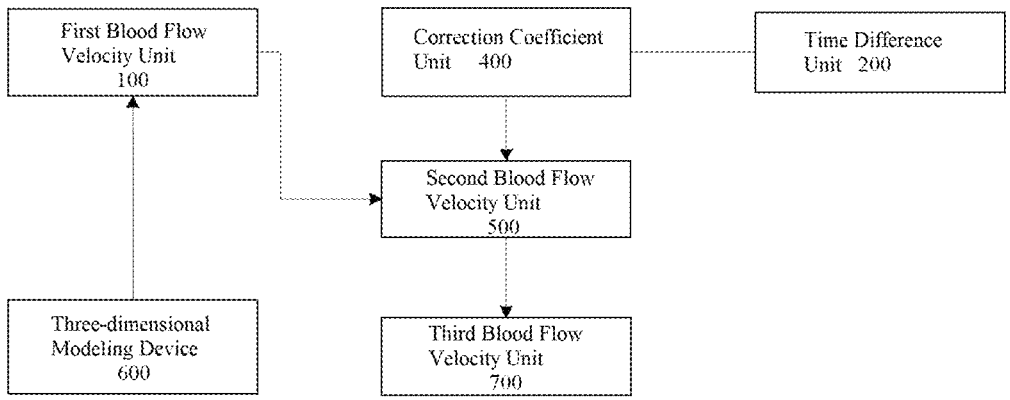
Figure 21:
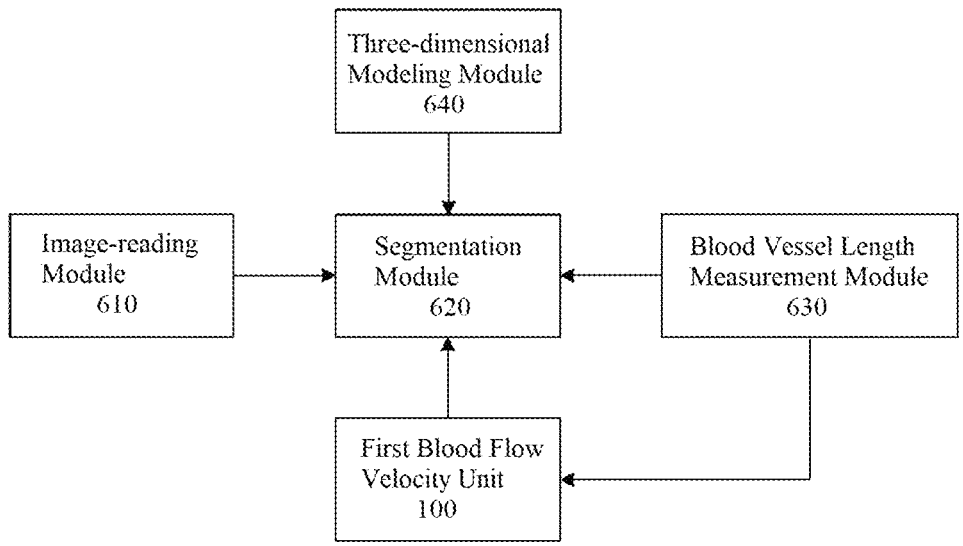

The left picture of FIG. 14 is a graph of length and diameter of a blood vessel;

FIG. 15 is a three-dimensional structure drawing of a coronary artery generated from FIG. 14 combined with body position angles and a centerline of the coronary artery;

FIG. 16 is a diagram showing the number of frames of a segmented image;

FIG. 17 is a diagram of coronary artery inlet pressure test;

FIG. 18 is a IMR test diagram;

FIG. 19 is a structural block diagram of an apparatus for correcting a blood flow velocity on the basis of angiogram images;

FIG. 20 is another structural block diagram of an apparatus for correcting a blood flow velocity on the basis of angiogram images;

FIG. 21 is a structural block diagram of a three-dimensional modeling device.

DETAILED DESCRIPTION OF PREFERRED EMBODIMENTS

In order to make the objectives, technical solutions and advantages of the disclosure clearer, the technical solutions of the disclosure will be clearly and completely described below with reference to the specific embodiments and corresponding drawings. It is apparent that the described embodiments are merely part of the embodiments of the disclosure rather than all of them. Based on the embodiments in the disclosure, without making creative work, all the other embodiments obtained by a person skilled in the art will fall into the protection scope of the disclosure.

Hereinafter, a number of embodiments of the present disclosure will be disclosed with drawings. For clear illustration, many practical details will be described in the following description. However, it should be understood that the present disclosure should not be limited by these practical details. In other words, in some embodiments of the present disclosure, these practical details are unnecessary. In addition, in order to simplify the drawings, some conventionally used structures and components will be shown in simple schematic ways in the drawings.

At present, a dosage of 5-10 ml contrast agent is used in most studies. After injecting the contrast agent, it takes an average time of 12-30 s that the coronary microcirculation restores from the hyperemia state to the baseline state. When performing a coronary artery examination, the surgeon will perform angiography from different body position angles for the detected blood vessels. Since it is different about the durations for adjusting the C-arm of an angiography machine to the specified angle each time, and it is also different about the start times for angiography, so that the flow velocity during each angiograph is affected by the fact that whether the coronary microcirculation after previous angiography restores to the baseline state.

Embodiment 1

Figure 1:
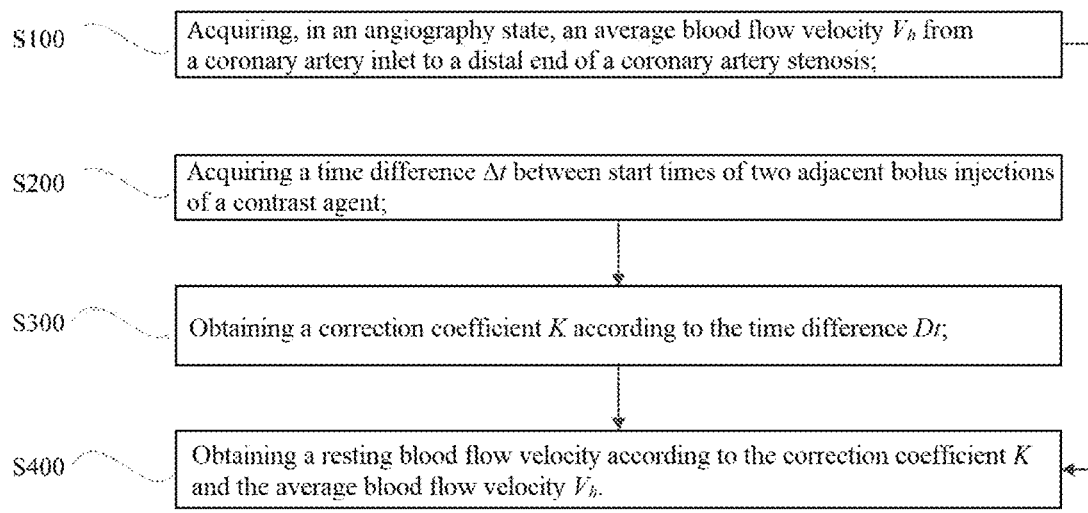
FIG. 1 is a flowchart of Embodiment 1 of the method for correcting a blood flow velocity on the basis of angiogram images of the present disclosure.

The flow velocity during each angiograph can be affected by the fact that whether the coronary microcirculation restores to the baseline state after previous angiography, to solve this problem, the disclosure, as shown in FIG. 1, provides a method for correcting a blood flow velocity on the basis of angiogram images comprising:

S100, acquiring, in an angiography state, an average blood flow velocity $V_h$ from a coronary artery inlet to a distal end of a coronary artery stenosis;

S200, acquiring a time difference $\Delta t$ between start times of two adjacent bolus injections of a contrast agent;

S300, obtaining a correction coefficient K according to the time difference $\Delta t$;

S400, obtaining a resting blood flow velocity $V_j$ according to the correction coefficient K and the average blood flow velocity $V_h$, with the specific formula being $V_j = V_h / K$.

In an embodiment of the present disclosure, there are four situations that affect K, specifically:

(1) if $\Delta t \geq 30$ s, then K=1;

(2) if 20 s$\leq \Delta t <$30 s, then $1 \leq K \leq 1.5$;

(3) if 10 s$< \Delta t <$20 s, then $1.5 < K < 2.0$;

(4) if $\Delta t \leq 10$ s, then K=2.

The disclosure provides a method for correcting a blood flow velocity on the basis of angiogram images, which comprises obtaining the correction coefficient K according to the time difference $\Delta t$, and obtaining the resting blood flow velocity $V_j$ according to the correction coefficient K and the average blood flow velocity $V_h$, so as to mitigate, in the prior art, the influence of whether the coronary microcirculation after previous angiography restores to the baseline state on the flow velocity during angiography.

In an embodiment of the present disclosure, the method of S100 comprises:

if acquiring $V_h$ by using a contrast agent delivery time algorithm, then: acquiring the number of frames of coronary angiogram images contained in a heartbeat cycle region, and acquiring a length of a blood vessel through which the contrast agent flows in the heartbeat cycle region;

calculating $V_h$ based on the formula $$V_h = \frac{L}{N/fps};$$

wherein, L represents the length of the blood vessel through which the contrast agent flows in the heartbeat cycle region; N represents the number of frames of coronary angiogram images contained in the heartbeat cycle region; and fps represents the number of frames transmitted per second, preferably, fps=15 frames/sec;

In an embodiment of the present disclosure, a manner for measuring the average blood flow velocity $\overline{V}$ comprises: contrast agent traversal distance algorithm, Stewart-Hamilton algorithm, First-pass distribution analysis method, optical flow method, or fluid continuity method.

In an embodiment of the present disclosure, a value range for L is 50-150 mm; or L=100 mm.

Embodiment 2

Figure 2:
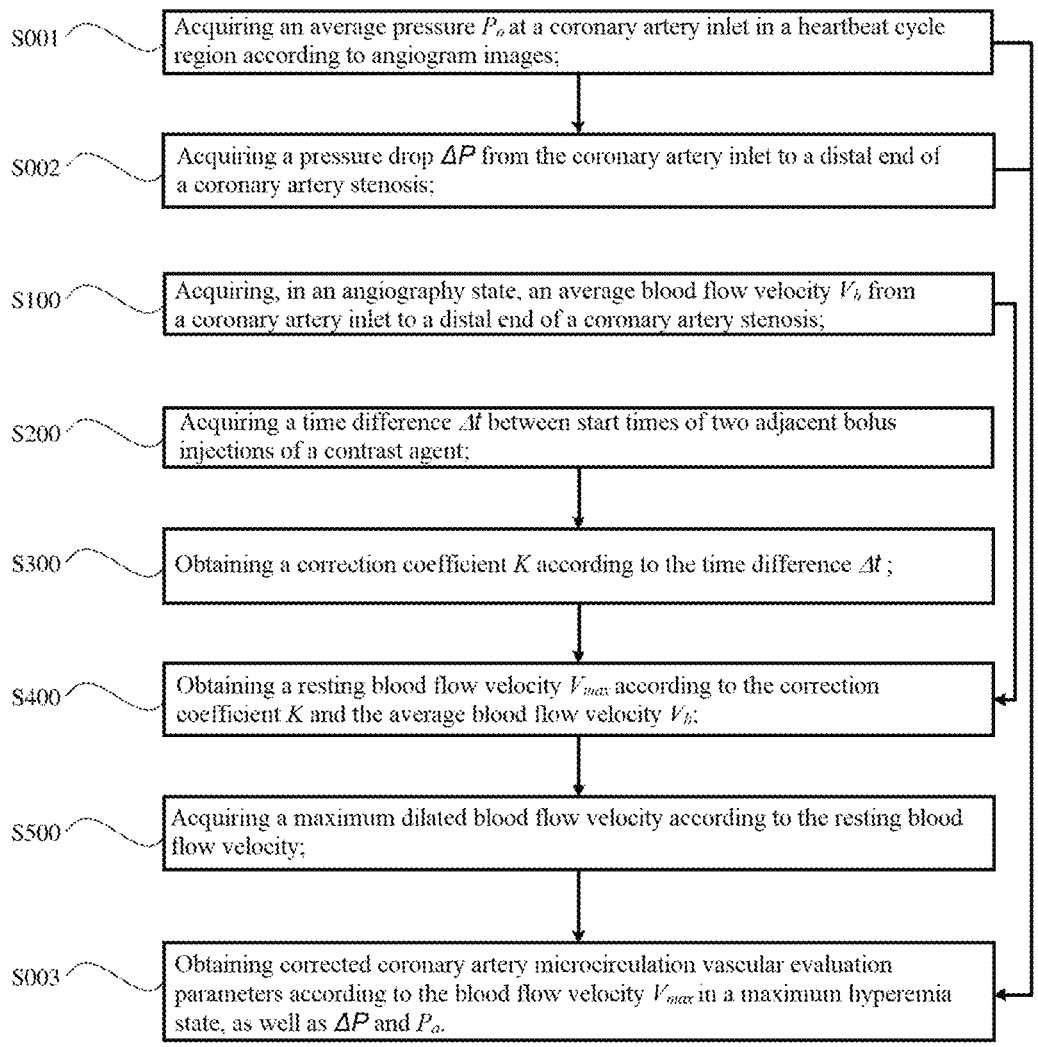
FIG. 2 is a flowchart of a method for correcting coronary microcirculation vascular evaluation parameters on the basis of angiogram images of the present disclosure.

As shown in FIG. 2, the present disclosure provides a method for correcting a maximum dilated blood flow velocity on the basis of angiogram images, comprising:

the above method for correcting a resting blood flow velocity on the basis of angiogram images;

S500: acquiring a maximum dilated blood flow velocity according to the resting blood flow velocity $V_j$, comprising: acquiring the maximum dilated blood flow velocity according to the formula $V_{max}=aV_j+b$; wherein $V_{max}$ represents the maximum dilated blood flow velocity, and a represents a constant with a value ranging from 1 to 3, and b represents a constant with a value ranging from 50 to 300.

Embodiment 2

As shown in FIG. 2, the present disclosure provides a method for correcting coronary microcirculation vascular evaluation parameters on the basis of angiogram images comprising:

S001: acquiring an average pressure $P_a$ at a coronary artery inlet in a heartbeat cycle region according to angiogram images, specifically by measuring $P_a$ in real-time with a blood pressure acquisition device;

S002: acquiring a pressure drop $\Delta P$ from the coronary artery inlet to a distal end of a coronary artery stenosis, comprising:

A. extracting coronary angiogram images of at least two body positions; preferably, the angle between the two body positions being equal to or greater than 30°; or in some embodiments, the angle being not specified;

B. denoising the coronary angiogram images, including: static noise removal and dynamic noise removal;

the static noise refers to the noise that is static over time, such as ribs in chest cavity.

the dynamic noise refers to the noise that varies over time, such as part of lung tissue and part of heart tissue, part of the dynamic noise being removed using mean filtering;

and comprising: further denoising by means of gray histogram analysis and utilizing threshold value.

Figure 3:
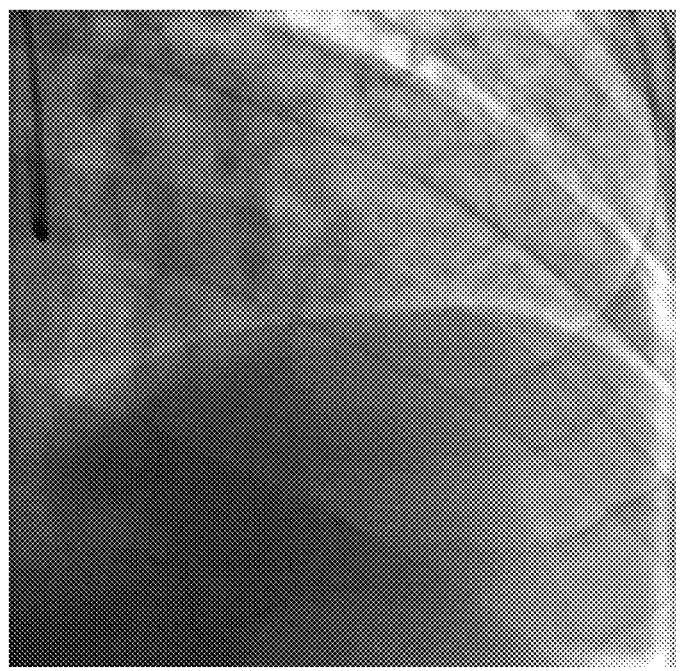
FIG. 3 is a reference image.
Figure 4:
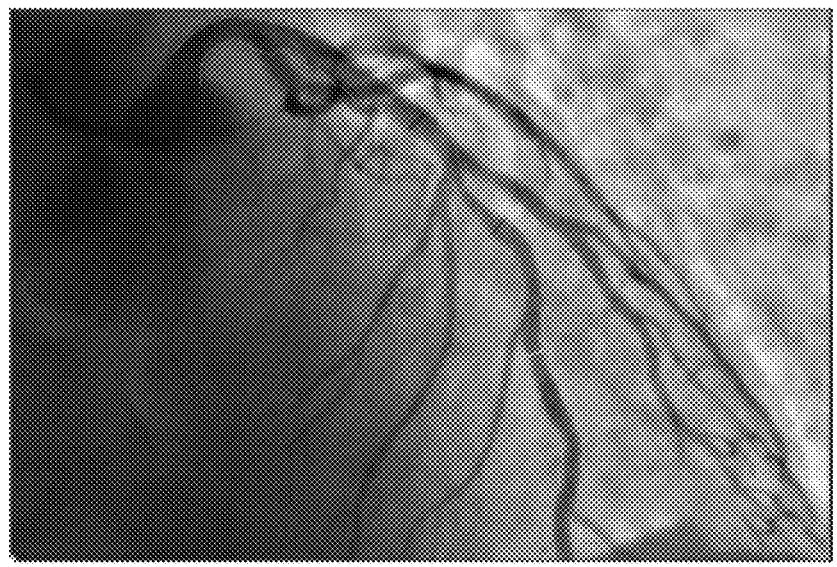
FIG. 4 is a target image to be segmented.
Figure 5:
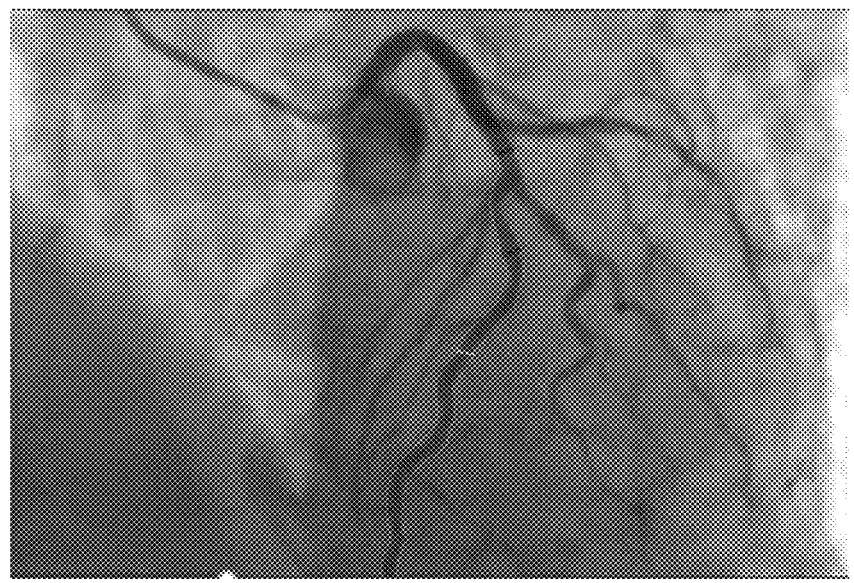
FIG. 5 is another target image to be segmented.
Figure 6:
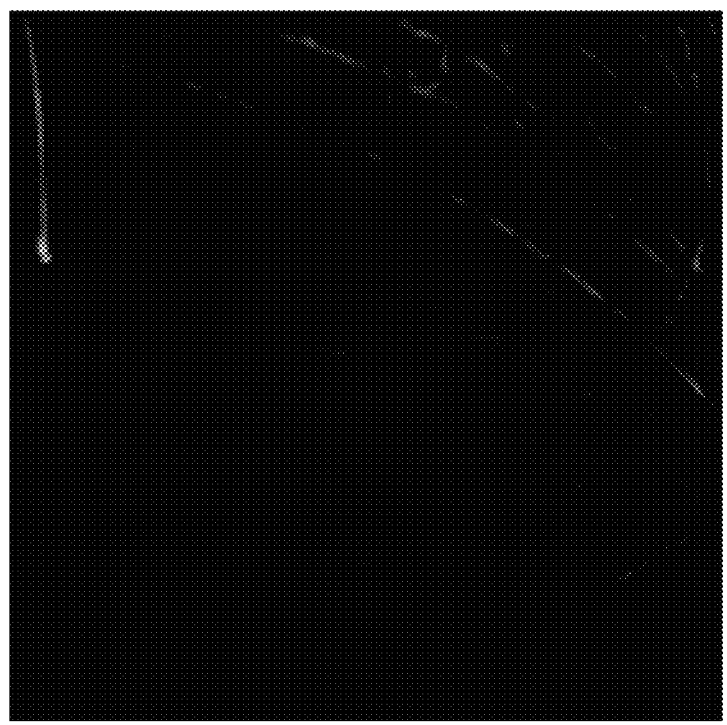
FIG. 6 is an enhanced catheter image.
Figure 7:
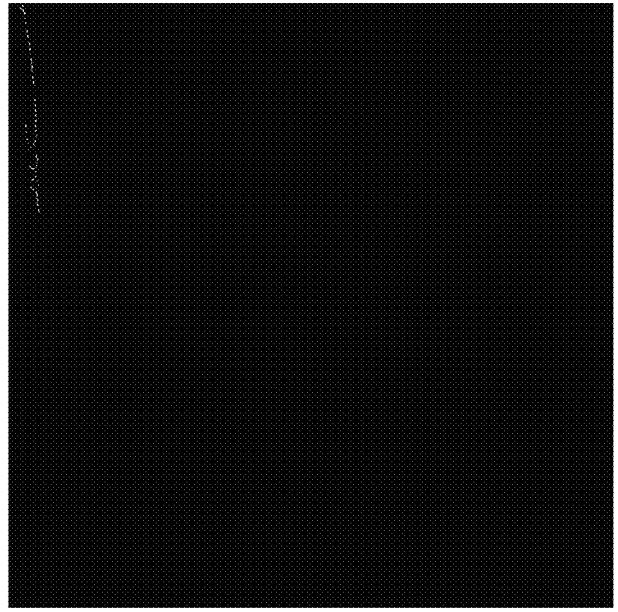
FIG. 7 is a binarized image of the feature points of the catheter.
Figure 8:
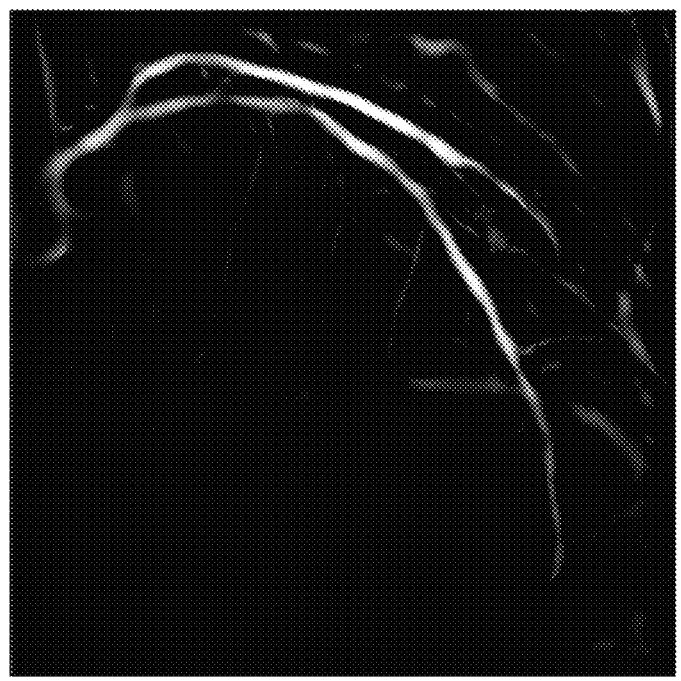
FIG. 8 is an enhanced target image.
Figure 9:
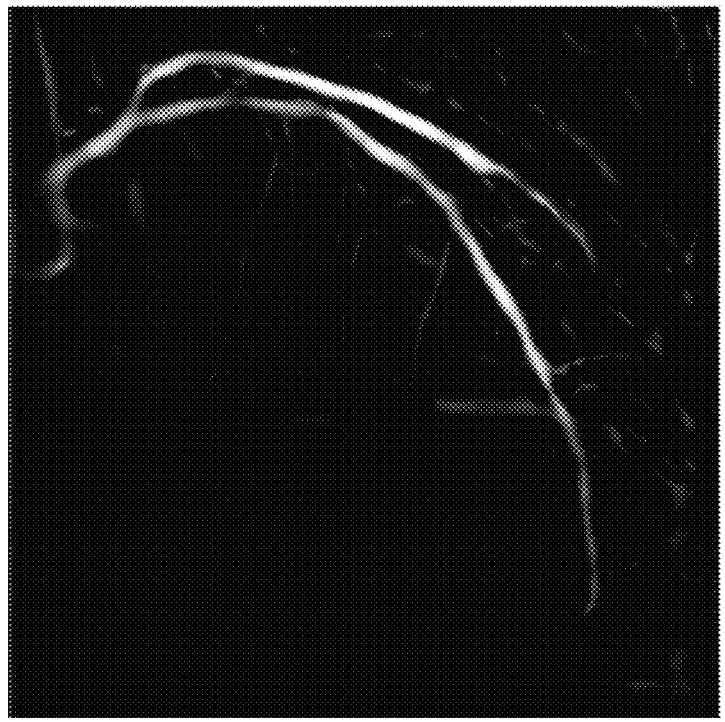
FIG. 9 is an image of the region where coronary arteries locate.
Figure 10:
FIG. 10 is a result image.
Figure 11:
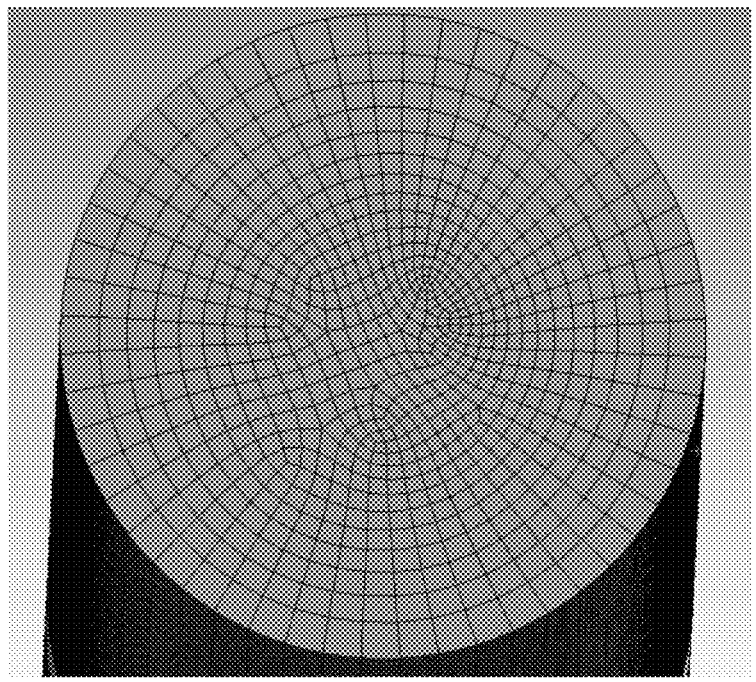
FIG. 11 is a screenshot of a cross section.
Figure 12:
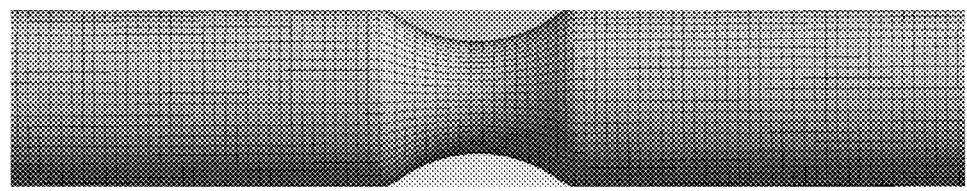
FIG. 12 is a screenshot of a longitudinal section.

C. removing interfering blood vessels in the coronary angiogram images to obtain a result image as shown in FIG. 10, comprising:

defining a first frame of a segmented image where a catheter appears as a reference image as shown in FIG. 3, and defining a k-th frame of the segmented image where a coronary artery appears completely as a target image as shown in FIGS. 4 and 5, wherein k is a positive integer greater than 1;

subtracting the target image shown in FIGS. 4 and 5 from the reference image shown in FIG. 3 to extract a feature point ○ of the catheter; subjecting the denoised image to image enhancement; subjecting the enhanced catheter image as shown in FIG. 6 to binarization processing to obtain a binarized image with a set of feature points ○ of the catheter as shown in FIG. 3;

subtracting the reference image as shown in FIG. 3 from the target image as shown in FIGS. 4 and 5; denoising, including static noise removal and dynamic noise removal; subjecting the denoised image to image enhancement using a multi-scale Hessian matrix; according to a positional relationship between each region in the enhanced target image as shown in FIG. 8 and the feature points of the catheter, determining and extracting an region of the coronary artery, that is, an image of the region where the coronary artery locates as shown in FIG. 9.

subjecting the image of the region where the coronary artery locates as shown in FIG. 9 to binarization processing to obtain a binarized coronary artery image;

subjecting the binarized coronary artery image to morphological operations, and using the feature points of the catheter as seed points, and carrying out dynamic region growth of the binarized coronary artery image according to the location of the seed point to obtain the result image as shown in FIG. 10;

D. extracting centerline and diameter of the coronary artery from each result image along an extension direction of the coronary artery;

E. projecting the centerline and diameter of each coronary artery on a three-dimensional space for three-dimensional modeling to obtain a three-dimensional structure of the coronary artery, comprising: acquiring the body position angle for taking each of the coronary angiogram images; projecting the centerline of each coronary artery in combination with the body position angle, a length L of a blood vessel and a diameter D of the blood vessel on the three-dimensional space, then generating the three-dimensional structure of the coronary artery;

F. subjecting the three-dimensional structure of the coronary artery to a grid division, as shown in FIGS. 11 and 12; based on the reconstructed three-dimensional structure of the coronary artery, an embodiment of the present disclosure uses a standard sweeping method to perform the grid division to generate a structural three-dimensional hexahedral grid; further, based on the reconstructed three-dimensional model of the coronary artery, the disclosure may also use other methods (such as segmentation method, hybrid method) to perform the grid division to generate the structured three-dimensional hexahedral grid;

G. using the centerline of the coronary artery as a longitudinal axis, dividing the grid into m points along the centerline of the coronary artery, and dividing the cross section corresponding to each point in the centerline of the coronary artery into n nodes, $\Delta P_i$ representing an average of the pressures of all nodes on the cross section of the i-th point in the centerline of the coronary artery, namely the pressure drop $\Delta P$ from the coronary artery inlet to the distal end of the coronary artery stenosis;

calculating the pressure drop $\Delta P_i$ using the following formula:

$$\Delta P_i = \frac{\sum_{1}^{n}(P_1 + P_2 + \ldots + P_n)}{n}$$

wherein $P_1$ represents the pressure of a first node on the cross section of the i-th point in the grids of the three-dimensional structure, $P_2$ represents the pressure of a second node on the cross section of the i-th point in the grids of the three-dimensional structure, $P_n$ represents the pressure of a n-th node on the cross section of the i-th point, both m and n are positive integers; the pressure $P_n$ is calculated by the Navier-Stokes equation;

S003, obtaining corrected coronary microcirculation vascular evaluation parameters according to the maximum dilated blood flow velocity $V_{max}$, $\Delta P$ and $P_a$ in Embodiments 1 to 3.

If the coronary microcirculation vascular evaluation parameter is an index of microcirculatory resistance IMR, then IMR=$(P_a-\Delta P)\times L/V_{max}$.

In the disclosure, the IMR value obtained by the maximum dilated blood flow velocity $V_{max}$ is more accurate, reducing the influence of the previous angiography time and a bolus injection pressure during the bolus injection of the contrast agent on the accuracy of the calculation of IMR value.

Embodiment 6

As shown in FIG. 19, the present disclosure provides an apparatus for correcting blood flow velocity on the basis of angiogram images comprising: a first blood flow velocity unit 100, a time difference unit 200, a correction coefficient unit 400, and a second blood flow velocity unit 500; the first blood flow velocity unit 100 is connected to the second blood flow velocity unit 500, and the correction coefficient unit 400 is connected to the time difference unit 200 and the second blood flow velocity unit 500, respectively; the first blood flow velocity unit 100 is configured to acquire, in an angiography state, an average blood flow velocity $V_h$ from a coronary artery inlet to a distal end of a coronary artery stenosis; the time difference unit 200 is configured to acquire a time difference $\Delta t$ between start times of two adjacent bolus injections of a contrast agent; the correction coefficient unit 400 is configured to receive the time difference $\Delta t$ transmitted by the time difference unit 200 to obtain a correction coefficient K; the second blood flow velocity unit 500 is configured to receive the average blood flow velocity $V_h$ sent by the first blood flow velocity unit 100 and the correction coefficient K sent by the correction coefficient unit 400, and to obtain the resting blood flow velocity $V_j$ according to the correction coefficient K and blood flow Velocity $V_h$.

As shown in FIG. 20, an embodiment of the present disclosure further comprises: a three-dimensional modeling device 600 connected to the first blood flow velocity unit 100. The three-dimensional modeling device is configured to read coronary angiogram images, select one heartbeat cycle region of the coronary angiography images, measure a length L of a blood vessel in the heartbeat cycle region, and perform three-dimensional modeling to obtain a three-dimensional structure of the coronary artery.

As shown in FIG. 21, in an embodiment of the present disclosure, the three-dimensional modeling device 600 comprises an image-reading module 610, a segmentation module 620, a blood vessel length measurement module 630, and a three-dimensional modeling module 640. The segmentation module 620 is connected to the image-reading module 610, the blood vessel length measurement module 630 and the three-dimensional modeling module 640, respectively. The blood vessel length measurement module 630 is connected to the first blood flow velocity unit 100. The image-reading module 610 is configured to read the angiogram images; the segmentation module 620 is configured to select one heartbeat cycle region of the coronary angiogram images; the blood vessel length measurement module 630 is configured to measure a length L of a blood vessel in the heartbeat cycle region, and transmit the length L of the blood vessel to the first blood flow velocity unit 100; the three-dimensional modeling module 640 is configured to subject the coronary angiogram images selected by the segmentation module 620 to three-dimensional modeling so as to obtain the three-dimensional structure of the coronary artery.

Embodiment 7

As shown in FIG. 21, the present disclosure provides an apparatus for correcting a maximum dilated blood flow velocity on the basis of angiogram images, comprising: the apparatus for correcting a blood flow velocity on the basis of angiogram images in Embodiment 6, and a third blood flow velocity unit 700 connected to the above apparatus for correcting a blood flow velocity on the basis of angiogram images; the third blood flow velocity unit 400 is configured to acquire the maximum dilated blood flow velocity $V_{max}$ according to the resting blood flow velocity $V_j$.

An embodiment of the present disclosure further comprises a coronary artery microcirculation vascular evaluation parameter measurement device connected to the third blood flow velocity unit 400, and a pressure drop measurement module connected to the coronary artery microcirculation vascular evaluation parameter measurement device.

Figure 13:
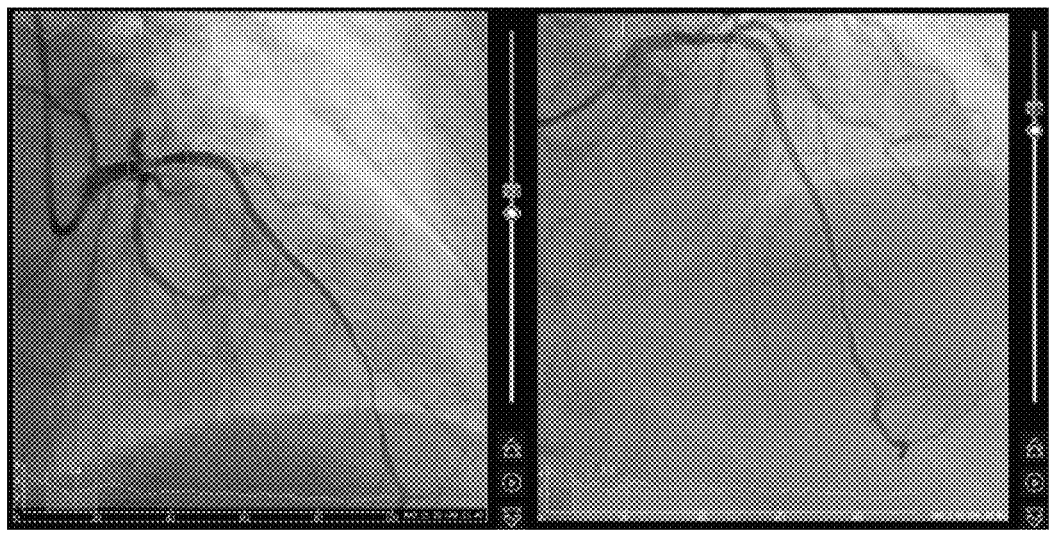
FIG. 13 shows angiogram images of two body positions.

The disclosure will be specifically described below in conjunction with specific examples:

FIG. 13 shows coronary angiogram images of two body positions taken for a patient; the body position angle of the left image is a right anterior oblique position RAO: 25° and a head position CRA: 23°; the body position angle of the right image is a right anterior oblique position RAO: 3° and a head position CRA: 30°;

As shown in FIG. 14, the length L of the blood vessel of the three-dimensional structure of the coronary artery=120 mm; the generated three-dimensional structure of the coronary artery is shown in FIG. 15;

the diameter D of the blood vessel=2~4 mm;

As shown in FIG. 16, $$V_h = \frac{L}{N/fps} = 120/[(11-5)/15] = 300;$$

Since the time difference between start times of the two adjacent bolus injection of the contrast agent is 20 s≤$\Delta t$<30 s, the value is taken as 1.1 for K, Therefore, $V_j$=300/1.1=272.7;

$V_{max}$=272.7+295=567.7

As shown in FIG. 17, $P_a$=100 mmHg;

As shown in FIG. 18, $\Delta P$=7, therefore, IMR=(100−7)× 120/567.7=19.66; if not corrected, the calculated IMR= (100−7)×120/(300+295)=18.75;

Therefore, it can be seen that the difference between the IMR measurement results before and after the correction by the coefficient K is 0.91, which is a large error. Therefore, it is necessary to use the coefficient to correct the blood flow velocity to obtain more accurate microcirculation vascular evaluation parameters, thereby improving the accuracy of measurement results.

The present disclosure provides a coronary artery analysis system, which comprises a base body, a blood pressure acquisition device and the above apparatus for correcting a maximum dilated blood flow velocity on the basis of angiogram images, both the last two being arranged on the base body. The pressure drop measurement module, the blood pressure acquisition device and the apparatus for correcting a maximum dilated blood flow velocity on the basis of angiogram images are all connected with the coronary microcirculation vascular evaluation parameter measurement device.

The present disclosure provides a computer storage medium having stored thereon a computer program to be executed by a processor, and the aforementioned method for correcting a resting blood flow velocity on the basis of angiogram images is implemented when the computer program is executed by the processor.

A person skilled in the art knows that various aspects of the present disclosure can be implemented as a system, a method, or a computer program product. Therefore, each aspect of the present disclosure can be specifically implemented in the following forms, namely: complete hardware implementation, complete software implementation (including firmware, resident software, microcode, etc.), or a combination of hardware and software implementations, which can be collectively referred to as "circuit", "module" or "system". In addition, in some embodiments, various aspects of the present disclosure may also be implemented in the form of a computer program product in one or more computer-readable media, and the computer-readable medium contains computer-readable program code. Implementation of method and/or system of embodiments of the present disclosure may involve performing or completing selected tasks manually, automatically, or a combination thereof.

For example, hardware for performing selected tasks according to the embodiment(s) of the present disclosure may be implemented as a chip or a circuit. As software, selected tasks according to the embodiment(s) of the present disclosure can be implemented as a plurality of software instructions executed by a computer using any suitable operating system. In the exemplary embodiment(s) of the present disclosure, a data processor performs one or more tasks according to the exemplary embodiment(s) of a method and/or system as described herein, such as a computing platform for executing multiple instructions. Optionally, the data processor comprises a volatile memory for storing instructions and/or data, and/or a non-volatile memory for storing instructions and/or data, for example, a magnetic hard disk and/or movable medium. Optionally, a network connection is also provided. Optionally, a display and/or user input device, such as a keyboard or mouse, are/is also provided.

Any combination of one or more computer readable media can be utilized. The computer-readable medium may be a computer-readable signal medium or a computer-readable storage medium. The computer-readable storage medium may be, for example, but not limited to, an electrical, magnetic, optical, electromagnetic, infrared, or semiconductor system, apparatus, or device, or any combination of the above. More specific examples (non-exhaustive list) of computer-readable storage media would include the following:

Electrical connection with one or more wires, portable computer disk, hard disk, random access memory (RAM), read only memory (ROM), erasable programmable read only memory (EPROM or flash memory), optical fiber, portable compact disk read only memory (CD-ROM), optical storage device, magnetic storage device, or any suitable combination of the above. In this document, the computer-readable storage medium can be any tangible medium that contains or stores a program, and the program can be used by or in combination with an instruction execution system, apparatus, or device.

The computer-readable signal medium may include a data signal propagated in baseband or as a part of a carrier wave that carries computer-readable program code. This data signal for propagation can take many forms, including but not limited to electromagnetic signals, optical signals, or any suitable combination of the above. The computer-readable signal medium may also be any computer-readable medium other than the computer-readable storage medium. The computer-readable medium can send, propagate, or transmit a program for use by or in combination with the instruction execution system, apparatus, or device.

The program code contained in the computer-readable medium can be transmitted by any suitable medium, including, but not limited to, wireless, wired, optical cable, RF, etc., or any suitable combination of the above.

For example, any combination of one or more programming languages can be used to write computer program codes for performing operations for various aspects of the present disclosure, including object-oriented programming languages such as Java, Smalltalk, C++, and conventional process programming languages, such as "C" programming language or similar programming language. The program code can be executed entirely on a user's computer, partly on a user's computer, executed as an independent software package, partly on a user's computer and partly on a remote computer, or entirely on a remote computer or server. In the case of the remote computer, the remote computer can be connected to a user's computer through any kind of network including a local area network (LAN) or a wide area network (WAN), or it can be connected to an external computer (for example, connected through Internet provided by an Internet service provider).

It should be understood that each block of the flowcharts and/or block diagrams and combinations of blocks in the flowcharts and/or block diagrams can be implemented by computer program instructions. These computer program instructions can be provided to the processor of general-purpose computers, special-purpose computers, or other programmable data processing devices to produce a machine, which produces a device that implements the functions/actions specified in one or more blocks in the flowcharts and/or block diagrams when these computer program instructions are executed by the processor of the computer or other programmable data processing devices.

It is also possible to store these computer program instructions in a computer-readable medium. These instructions make computers, other programmable data processing devices, or other devices work in a specific manner, so that the instructions stored in the computer-readable medium generate an article of manufacture comprising instructions for implementation of the functions/actions specified in one or more blocks in the flowcharts and/or block diagrams.

Computer program instructions can also be loaded onto a computer (for example, a coronary artery analysis system) or other programmable data processing equipment to facilitate a series of operation steps to be performed on the computer, other programmable data processing apparatus or other apparatus to produce a computer-implemented process, which enable instructions executed on a computer, other programmable device, or other apparatus to provide a process for implementing the functions/actions specified in the flowcharts and/or one or more block diagrams.

The above specific examples of the present disclosure further describe the purpose, technical solutions and beneficial effects of the present disclosure in detail. It should be understood that the above are only specific embodiments of the present disclosure and are not intended to limit the present disclosure. Within the spirit and principle of the present disclosure, any modification, equivalent replacement, improvement, etc. shall be included in the protection scope of the present disclosure.

What is claimed is:

1. A method for correcting a resting blood flow velocity on the basis of an interval time between angiogram images, comprising:
   acquiring, in an angiography state, an average blood flow velocity $V_h$ from a coronary artery inlet to a distal end of a coronary artery stenosis;
   acquiring a time difference $\Delta t$ between start times of two adjacent bolus injections of a contrast agent;
   obtaining a correction coefficient K according to the time difference $\Delta t$;
   obtaining a resting blood flow velocity $V_j$ according to the correction coefficient K and the average blood flow velocity $V_h$.

2. The method for correcting a resting blood flow velocity on the basis of an interval time between angiogram images according to claim 1, wherein a manner for obtaining a resting blood flow velocity $V_j$ according to the correction coefficient K and the average blood flow velocity $V_h$ comprises:
   obtaining the resting blood flow velocity $V_j$ according to the formula $V_j = V_h/K$.

3. The method for correcting a resting blood flow velocity on the basis of an interval time between angiogram images according to claim 1, wherein a manner for obtaining a correction coefficient K according to the time difference $\Delta t$ comprises:
   if $\Delta t \geq 30$ s, then K=1;
   if $20 \leq \Delta t < 30$ s, then $1 < K \leq 1.5$;
   if $10 \leq \Delta t < 20$ s, then $1.5 < K < 2.0$;
   if $\Delta t \leq 10$ s, then K=2.

4. The method for correcting a resting blood flow velocity on the basis of an interval time between angiogram images according to claim 1, wherein a manner for acquiring, in an angiography state, an average blood flow velocity $V_h$ from a coronary artery inlet to a distal end of a coronary artery stenosis comprises:
   acquiring the number of frames of coronary angiogram images contained in a heartbeat cycle region;

$$V_h = \frac{L}{N/fps}$$

wherein, L represents a length of a blood vessel through which a contrast agent flows in the heartbeat cycle region; N represents the number of frames of the coronary angiogram images contained in the heartbeat cycle region; and fps represents the number of frames transmitted per second.

5. The method for correcting a resting blood flow velocity on the basis of an interval time between angiogram images according to claim 4, wherein a value range for L is 50-150 mm; or L=100 mm.

6. The method for correcting a resting blood flow velocity on the basis of an interval time between angiogram images according to claim 1, wherein a manner for measuring the average blood flow velocity $V_h$ comprises:
   contrast agent traversal distance algorithm, Stewart-Hamilton algorithm, First-pass distribution analysis method, optical flow method, or fluid continuity method.

7. An apparatus for correcting a resting blood flow velocity on the basis of an interval time between angiogram images, for using in the method for correcting a resting blood flow velocity on the basis of angiogram images according to claim 1, comprising: a first blood flow velocity unit, a time difference unit, a correction coefficient unit and a second blood flow velocity unit; the first blood flow velocity unit being connected to the second blood flow velocity unit, and the correction coefficient unit being connected to the time difference unit and the second blood flow velocity unit, respectively;
   the first blood flow velocity unit being configured to acquire, in an angiography state, an average blood flow velocity $V_h$ from a coronary artery inlet to a distal end of a coronary artery stenosis;
   the time difference unit being configured to acquire a time difference $\Delta t$ between start times of two adjacent bolus injections of a contrast agent;
   the correction coefficient unit being configured to receive the time difference $\Delta t$ transmitted by the time difference unit to obtain a correction coefficient K;
   the second blood flow velocity unit being configured to receive the average blood flow velocity $V_h$ in the angiography state sent by the first blood flow velocity unit and the correction coefficient K sent by the correction coefficient unit, and to obtain the resting blood flow velocity $V_j$ according to the correction coefficient K and the average blood flow velocity $V_h$.

8. A non-transitory computer storage medium having stored thereon a computer program to be executed by a processor, wherein the method for correcting a resting blood flow velocity on the basis of an interval time between angiogram images according to claim 1 is implemented when the computer program is executed by the processor.

* * * * *